(12) United States Patent
Moll et al.

(10) Patent No.: US 8,485,998 B2
(45) Date of Patent: Jul. 16, 2013

(54) BLOOD TREATMENT SYSTEM

(75) Inventors: Stefan Moll, Melsungen (DE); Gerhard Bock, Friedewald (DE); Sándor Dolgos, Szentendre (HU)

(73) Assignee: B. Braun Avitum AG, Melsungen (DE)

( * ) Notice: Subject to any disclaimer, the term of this patent is extended or adjusted under 35 U.S.C. 154(b) by 1153 days.

(21) Appl. No.: 11/961,499

(22) Filed: Dec. 20, 2007

(65) Prior Publication Data
US 2008/0176210 A1   Jul. 24, 2008

(30) Foreign Application Priority Data
Dec. 21, 2006   (EP) .................................... 06126930

(51) Int. Cl.
*A61M 37/00* (2006.01)

(52) U.S. Cl.
USPC ........................................ 604/5.01; 604/6.09

(58) Field of Classification Search
USPC .................. 604/4.01–5.04, 6.09, 28, 29, 507, 604/508, 65–67; 422/44–48; 210/645–650, 210/321.71–321.75; 128/898; 600/301
See application file for complete search history.

(56) References Cited

U.S. PATENT DOCUMENTS 6,673,314 B1 * 1/2004 Burbank et al. ................. 422/44
2007/0235376 A1   10/2007 Daniel

* cited by examiner

*Primary Examiner* — Philip R Wiest
(74) *Attorney, Agent, or Firm* — RatnerPrestia

(57) ABSTRACT

A blood treatment system including a computer with a program library containing data sets for the functional processes of blood treatment apparatus. The computer is used to generate data sets with the aid of a catalog of questions to be responded to interactively. In this manner, data sets can be generated corresponding to the individual requirements. The selecting of a data set can also be performed corresponding to the individual needs of the users and patients, respectively.

30 Claims, 3 Drawing Sheets

50

Figure 1:
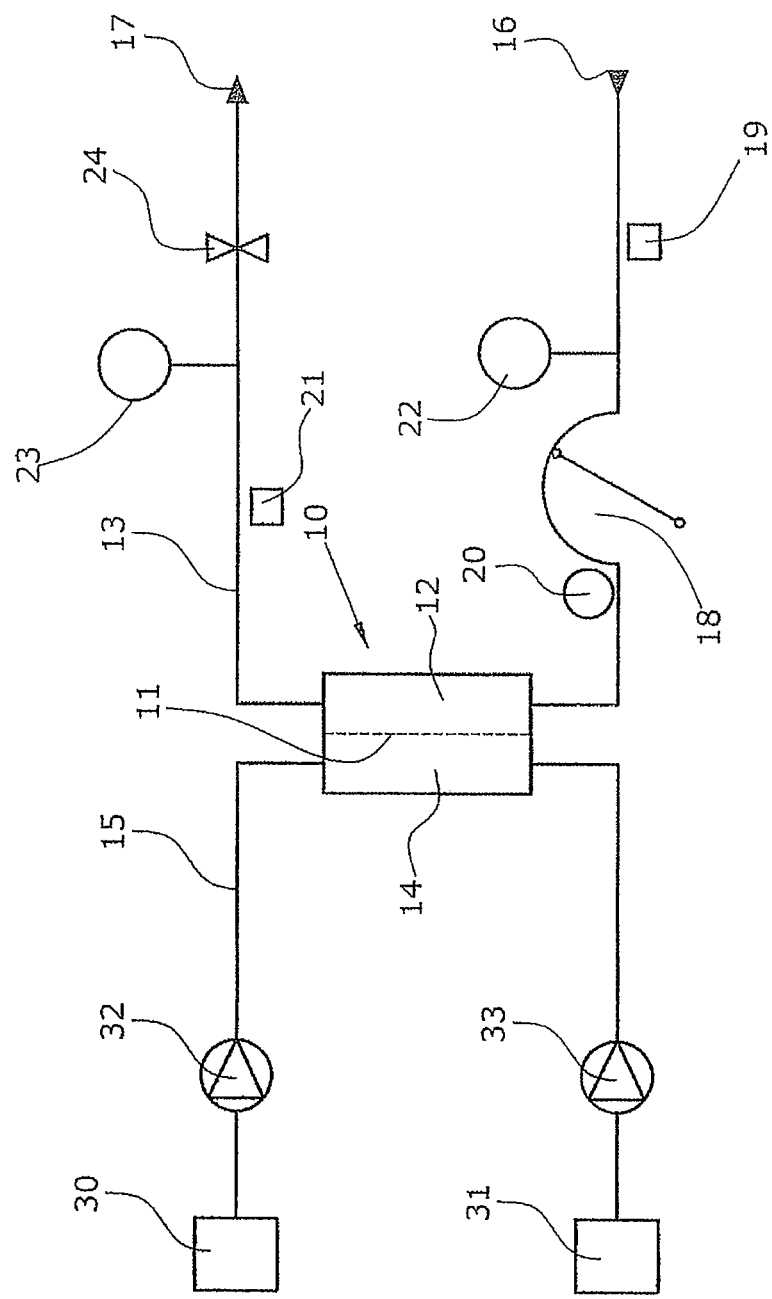

- Automatic switch-on
- Self-test, once per day
- HD treatment possible
- HDF treatment possible
- HF treatment possible
- Treatment corresponding to consumption material (RFID's)
- SN treatment possible
- Fixed irrigation procedure possible
- Fixed irrigation procedure dialyzer (blood side)
  - [XXX] Irrigation quantity
  - [XXX] Irrigation time
- Irrigation corresponding to consumption material (RFID's)
- Screen configuration corresponding to Nurse A
- Instruction for Nurse B (RFID's)
- Examination of concentrate (RFID's)
- Automatic transition to stand-by mode
- Stable setting of patient volume
- Measurement of blood pressure
  - [XXX] Measurement interval
- Taking of blood sample
- Automatic evacuation of to consumption material after disconnecting the patient
- Automatic transition from evacuation of consumption material to disinfection
- Disinfection
  - [XXX] Selection box
- Next Patient
- Automatic switch-off

Fig. 3

BLOOD TREATMENT SYSTEM

This application claims priority to European Patent Application No. 06 126 930.4, filed Dec. 21, 2006, which is incorporating herein by reference.

FIELD OF THE INVENTION

The present invention relates to a blood treatment system for extracorporeal blood treatment, including at least one blood treatment apparatus comprising a filter connected to a blood circuit and to a dialysate circuit, a control device for controlling functional processes, a user interface comprising a monitor and input devices.

BACKGROUND OF THE INVENTION

Known blood treatment systems such as e.g. dialysis apparatus are complex both in configuration and handling because they offer numerous options with regard to their setting and their program sequence. Thus, the operating personnel, hereunder briefly referred to as "users", has to be specifically trained. The type of treatment which can be performed by a blood treatment apparatus comprises diverse phases. These include e.g. the preparation of the apparatus; the connecting of the patient to the apparatus, e.g. establishing a connection between the patient and the tube system of the apparatus; the actual therapy, e.g. the purification of the blood; and the after-treatment concluding the therapy, e.g. by administering specific medicants.

In the use of blood treatment apparatus, two different strategies exist: The first strategy consists in that the user will select the respective next step of the treatment process on the apparatus on the basis of his or her experiences. According to the second strategy, an automatic program sequence is provided wherein the blood treatment apparatus will detect the current state of a program sequence by means of sensors and after termination of a treatment step will positively carry out the next program step.

DE 103 23 843 A1 describes a concept wherein various temporal modes of a blood treatment are visually represented on a touch screen, allowing the user to perform a selection among them. The respective temporal mode currently in operation is identified by a control device and specifically represented on the touch screen. The end of a temporal mode will be detected in order to automatically initiate the start of the subsequent temporal mode. In this concept, the modes are processed according to a fixed temporal order. As soon as the sensors detect a given mode, an automatic transition to the next mode will take place. What is realized in this concept is a rigid sequence of functions, allowing no possibility to the user to change the pre-stored program. This shortcoming causes a massive restriction of flexibility since the dialysis apparatus will automatically and rigidly follow a presumably ideal sequence. Possible exceptional situations as they may occur ever again in various patients, cannot be considered. The fixed program sequence will confine the range of user interventions within the limits of a rigid system.

A fixedly predetermined sequence of the individual steps entails a massive restriction of flexibility. Since the blood treatment apparatus rigidly operates according to a presumably ideal sequence which is carried out automatically, possible special situations as may occur in various patients, or typical processes inherent in the culture of a given country and having their origin in the country's local customs or legal requirements, or also hospital-specific routines, can thus be considered only insufficiently.

To guarantee a more-individual and nonetheless automated concept of the functional process of the apparatus, some manufacturers have adopted an approach to the effect that, in some processes, a selection among various options is allowed. Thus, for instance, it can be decided whether, at the end of the therapy, the dialyzer is to be evacuated immediately and automatically or whether the evacuation is to start only upon manual activation via a special input key. Similar choices can be made with respect to the evacuating of the bicarbonate cartridge or an optional subsequent disinfection.

For safety reasons, the possible selection and respectively activation of the functionality can be performed only by a service technician or through input via menus requiring separate access. Disadvantageously, in this solution, the individual selection of the behavior during specific steps will be unintelligible to the health-care personnel, entailing the loss of a comprehensive survey on the overall process. Further, in the use of this apparatus, a mutual coordination between the nurse, the physician and the technician must be carried out. A process which has been modified at individual points will then be unfit for individual adaptation to respective days, patients and consumption materials and will have been installed only on the blood treatment apparatus configured for such a process.

In one aspect, the present invention provides a blood treatment system which makes it possible for the user to adapt the whole treatment process to special requirements, such as e.g. the treatment standard of a dialysis center, the available consumption material or the demands posed by the patient. The possibility for the user to survey the whole functional process of the treatment is to be maintained, and it is to be reliably precluded that settings could be performed which would be nonsensical or even dangerous to the patient. In another aspect, the invention provides a blood treatment system wherein the designing of the whole functional process from switch-on of the apparatus up to the disinfecting of the tube system and the apparatus components can be performed on the blood treatment system itself and/or on a separate computer.

The blood treatment system of the present invention includes a program library is provided which includes various functional processes in the form of data sets for the operation of the blood treatment apparatus, and that respectively one data set can be selected to be activated for a treatment process.

SUMMARY OF THE INVENTION

According to an aspect of the invention, there is provided a program library wherein the programs contained therein either have been predetermined or can be generated by the user, possibly assisted by an adviser. Provided for this purpose is an input program which contains questions about the intended operational process, offering the possibility to enter parameters via the monitor surface from which the functional process and the appertaining data set can then be generated in the computer. Thus, functional processes can be generated with respect to the date, or a specific consumption material such as tubes, dialysate or additional medicants, all of these in relation to the patient. A functional process can be understood to be the overall therapeutic process or also just a part of the therapeutic process. In the latter case, standardized process components can be assembled into a complete functional process.

According to a preferred embodiment of the invention, a device is provided for generating a functional process to be included in the program library, said device comprising a monitor screen surface presenting a catalog of questions to be answered interactively by the user. The input program visually indicates various options and further points out the consequences resulting therefrom. In this manner, the user—assisted, if required, by a service technician—can establish an individual functional process and place it in the program library. For the health-care personnel, the handling of the blood treatment apparatus is reduced to those operating steps which are absolutely required.

The functional process includes unambiguous decisions (i.e. decisions not dependent on conditions) such as e.g. the switch-on of the apparatus in the morning according to a yes/no alternative. Apart from this, it is also possible to define processes which depend on specific conditions, for instance: If the apparatus is operated by Nurse A, the disinfection shall not start automatically whereas, in case of Nurse B, automatic start of disinfection can be performed. To be counted among the further factors which influence the functional process are e.g. the respective patient undergoing the treatment whose identification code will be input into the computer of the blood treatment apparatus, or the user's person whose identification code will also be input into the computer, e.g. by a transponder or a machine-readable personnel card. Further, the selection of the functional process can be influenced by the time (time of day or calendar date) or the consumption materials used; these conditions can be read in by a transponder.

When the functions to be included into the functional process have been selected, the consequences of the selection are detected in the computer and displayed. Such consequences can be e.g. the lengths of the preparation times, the quantity of consumption of dialysate, or required actions on the side of the user.

After a functional process has been generated, the preparation program will generate therefrom a set of configuration data which is readable by the blood treatment apparatus. This configuration data set will be provided with an identification and can then be used in each of the blood treatment apparatus belonging to the treatment system. Thus, the data sets of different functional processes can be copied to the control devices of a plurality of blood treatment apparatus.

From the catalog of questions answered on the computer, there is automatically generated the data set consisting of the configuration data. Installation of such data sets on the blood treatment apparatus can be performed by use of a data carrier or via network connection. This can be carried out at one point of time or continuously. It is possible to store a plurality of different data sets in one blood treatment apparatus, and the data set to be activated in the given case will be selected at the start of the therapy or during the therapy. The selection of the data set can be performed by the user via the monitor or in an automated manner, e.g. in dependence on a patient card or a machine-readable user identification, as well as in dependence on the selected form of therapy or the consumption materials used.

This makes it possible that a therapy will comprise an individual but previously defined and optimized process. If desired, it is also possible to assign to each user (nurse) an individually preferred treatment process, or to assign to especially critical patients a process which includes only few automatisms and thus involves considerable presence and attention on the nurse's side.

The consumption articles of the blood treatment apparatus include, apart from the tube system, also the filter or the dialyzer. If the control device of the apparatus has knowledge of the consumption articles specified according to type and size, it will then be possible to perform the irrigation and filling process depending on the consumption articles used. In "high-flux dialyzers", for instance, one will select a different irrigation and filling process than in "low flux dialyzers". Thereby, time and irrigation liquid will be saved.

Normally, it will be sufficient if a small number of data sets is put at the disposal of the dialysis center or the operator of several dialysis centers and if the corresponding data sets are made available on all blood treatment apparatus. The data set to be used can then be selected in situ in dependence on sensor signals and/or by manual operation or input.

Reasonably, one should tend to put a larger number of data sets and thus functional processes to the disposal of an experienced user than to an average-skilled nurse. The latter kind of users will be given a restricted range of options. In this manner, very specific and optimized treatment processes can be used without entailing the risk of misguided operation by normal heath-care personnel.

The invention further relates to a method for operation of a blood treatment apparatus.

Advantageous embodiments and variants of the invention are set forth herein.

A preferred embodiment of the invention will be explained in greater detail hereunder with reference to the accompanying drawings.

BRIEF DESCRIPTION OF THE DRAWINGS (IF APPLICABLE)

Figure 2:
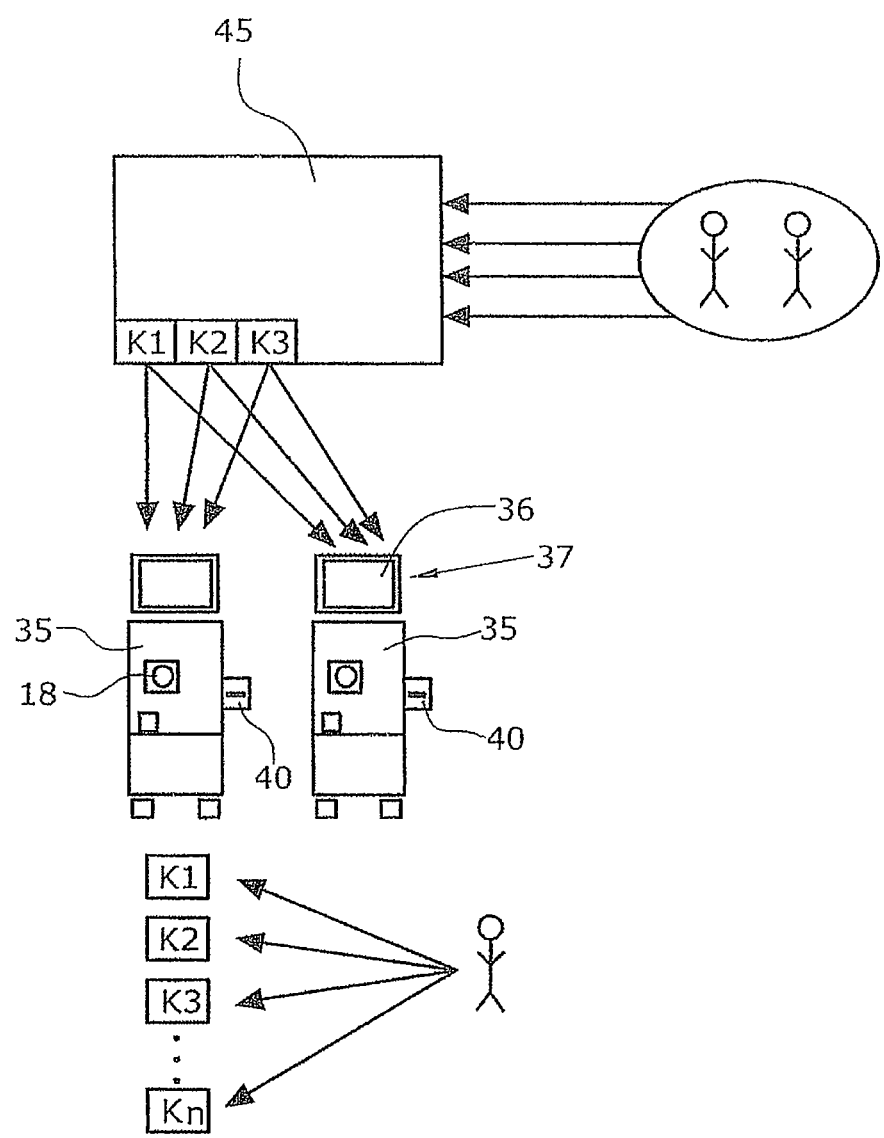

FIG. 1 is a schematic representation of a blood treatment apparatus;

FIG. 2 is a schematic representation illustrating the cooperation between a separate computer and a blood treatment system including a plurality of blood treatment apparatus; and FIG. 3 is a view of the configuration of a catalog of questions generated on a touchscreen for interactive input of answers for the purpose of establishing a data set of a functional process of a blood treatment apparatus.

DETAILED DESCRIPTION OF THE INVENTION

The blood treatment apparatus illustrated in FIG. 1 is a dialysis apparatus comprising a dialyzer 10 including two chambers with a dialyzer membrane 11 arranged therebetween. The blood chamber 12 of the dialyzer is connected to a blood circuit 13, and the dialysate chamber 14 is connected to a dialysate circuit 15. Blood circuit 13 comprises a tube system with an inlet 16 and an outlet 17. The tube system is guided to pass through a blood pump 18 provided to perform a volumetric conveying process, with the flow rate being proportionate to the drive speed. Provided in blood circuit 13 are a plurality of sensors, notably a blood sensor 19 for detecting, by sensing the color of blood, the presence of blood in the tube system, a tube sensor 20 for detecting whether the tube has been correctly placed in the blood pump 18, an air sensor 21 for detecting the presence of air in the tube system, a pressure sensor 22 for measuring the arterial blood pressure and a pressure sensor 23 for measuring the venous blood pressure.

Blood pump 18 forms an actor existing in the blood circuit. A further actor is formed by a tube clamp 24 arranged in the venous conduit.

Dialysate circuit 15 is connected to a dialysate source 30 and a discharge means 31. The feed conduit includes a first pump 32 and the return conduit a second pump 33.

FIG. 2 shows two dialysis apparatus 35 which belong to the same dialysis system and are illustrative of any desired number of dialysis apparatus. Each dialysis apparatus 35 comprises a blood pump 18 on the front side of a housing. Arranged on top of the housing is a monitor 36 constituting the user interface 37. Internally of monitor 36, the control device of the blood treatment apparatus 35 is arranged.

Each blood treatment apparatus is provided with a reading device 40 which in the present example is configured as a card reader adapted to read a card in the form of a chip card. The chip cards are, on the one hand, user cards provided with an identification of a respective user and, on the other hand, patient cards provided with an identification of a respective patient. On the basis of a given identification, the control device of the apparatus can also receive information on the authorization and respectively the therapeutic needs of the respective person. Alternatively to the above reading devices 40, use can be made e.g. of transponder readers for contactless retrieval of information from a transponder worn on the respective person's body.

Further shown in FIG. 2 is an external computer 45 having stored therein a program library comprising numerous data sets, each of them corresponding to a functional process. The data sets $K_1, K_2, K_3$ are supplied from computer 45 to each of the blood treatment apparatus, either in wireless manner or via a wired network. The programs stored in the program library include, in addition to the configuration data sets, also user wishes and further information items.

The separate computer 45 is equipped with a touchscreen for interactive input of constraint conditions or of requirements. For this input process, the catalog of questions 50 shown in FIG. 3 is displayed on the touchscreen. For entering the respective condition or information, the user or adviser will mark the respective boxes. On the basis of the thus answered catalog of questions 50, the computer 45 generates a data set $K_n$ which is made available to the blood treatment apparatus 35. This data set forms the configuration data set indicating the procedural sequence of the operational program of blood treatment apparatus 35.

On the blood treatment apparatus 35, the respective data set $K_1 \ldots K_n$ is selectable by the user; alternatively, it can be determined with the aid of sensors provided to detect e.g. the type of the consumption articles used (dialyzer, tube system etc.) so that a selection of useful data sets is performed on the basis of this detection. The final selection of a data set can then be performed in dependence on other parameters such as e.g. the data of the user or of the patient, or through selection by hand.

In FIG. 3, RFID means "radio frequency identification". This term is meant to denote identifications which are retrievable in a wireless manner and are transmitted by transponder at a query station.

For establishing the data sets from the catalog of questions 50, the separate computer 45 receives a model of the blood treatment apparatus 35 which is adapted to have parameters entered thereinto and which will simulate a functional process with these parameters. Subsequent to such a functional process, the respective data set will be stored in the program library.

The sensors provided in the blood treatment apparatus can also be configured to detect and read "tags" attached to the consumption articles, and to mark the type of such tags so that the selection of the data set can be performed on this basis.

What is claimed is:

1. A blood treatment system for extracorporeal blood treatment, including at least one blood treatment apparatus comprising:
a filter connected to a blood circuit and to a dialysate circuit,
a control device for controlling functional processes,
a user interface comprising a monitor and input devices, wherein the user interface is configured to generate a screen display including a catalog of questions to be interactively answered by the user, and wherein the answers are used to generate a functional process that controls operation of the blood treatment apparatus, which is in the form of data sets, to be transmitted to and stored in a program library of various functional processes, each of which control operation of the blood treatment apparatus, that is remote from the user interface,
wherein respectively one data set can be selected to be activated for a treatment process based on input received via the user interface.

2. The blood treatment system of claim 1, wherein means are provided for graphic representation of the selected data set and its functional process, respectively.

3. The blood treatment system of claim 1, wherein, for each data set, consequential information items are generated and displayed.

4. The blood treatment system of claim 3, wherein the consequential information includes one or more of a preparation time, consumption of liquid and required user reactions.

5. The blood treatment system of claim 1, wherein the data set includes, apart from the functional process, also parameters of the monitor display.

6. The blood treatment system of claim 1, wherein a separate computer is provided which includes the program library and communicates with the control device of the blood treatment apparatus.

7. The blood treatment system of claim 6, wherein a portable data carrier is provided for communication between the program library and the blood treatment apparatus.

8. The blood treatment system of claim 6, wherein said separate computer is connected to a plurality of blood treatment apparatus via a communication network.

9. The blood treatment system of claim 6, wherein said separate computer is operative to run a model of the blood treatment apparatus, which model is adapted for input of parameters thereinto and operative to simulate a functional process with these parameters, and wherein the data sets of individual functional processes can be stored in the program library.

10. The blood treatment system of claim 1, wherein the blood treatment apparatus includes a plurality of data sets for selection among them.

11. The blood treatment system of claim 1, wherein an ID reader is provided for detecting an identification of a user, with the control device receiving a data set in dependence on the detected identification.

12. The blood treatment system of claim 1, wherein an ID reader is provided for detecting an identification of a patient, with the control device receiving a data set in dependence on the detected identification.

13. The blood treatment system of claim 1, wherein a sensor is provided for detecting the presence of a specific consumption article in the blood treatment apparatus, and the type of said article, with the control device selecting one or a plurality of data sets in dependence on the detection result.

14. The blood treatment system of claim 1, wherein means are provided for detecting the setting of a specific type of treatment on the blood treatment apparatus, with the control device selecting one or a plurality of data sets in dependence on the detection result.

15. The blood treatment system of claim 1, wherein the program library is included on a data carrier and, at start-up of the blood treatment apparatus, the contents of said data carrier are input into the control device of the blood treatment apparatus.

16. A method for operating a blood treatment apparatus including a filter connected to a blood circuit and to a dialysate circuit, a control device for controlling functional processes, a user interface comprising a monitor and input devices, the method comprising:
receiving input via the user interface;
generating a functional process in the form of a data set that controls operation of the blood treatment apparatus to be transmitted to and stored in a remote program library of various functional processes, each of which control operation of the blood treatment apparatus, by generating an input screen display at the user interface including a catalog of questions to be interactively answered by the user, wherein the remote program library includes various functional processes, each of which control operation of the blood treatment apparatus, in the form of data sets for the operation of the blood treatment apparatus based on the input, and
implementing a treatment process in accordance with the generated data set.

17. The method of claim 16, wherein said data set and its functional process, respectively, is graphically represented on the monitor.

18. The method of claim 16, wherein, for each data set, consequential information items are generated and displayed.

19. The method of claim 18, wherein the consequential information includes one or more of a preparation time, consumption of liquid and required user reactions.

20. The method of claim 16, wherein, apart from the functional process, parameters of the monitor display are also input into said data set.

21. The method of claim 16, wherein the program library is generated in a separate computer adapted to communicate with the control devices of the one or plural blood treatment apparatus.

22. The method of claim 21, wherein said communication is performed using a portable data carrier.

23. The method of claim 21, wherein said separate computer will be connected to a plurality of blood treatment apparatuses via a communication network.

24. The method of claim 21, wherein a model of the blood treatment apparatus is generated in said separate computer, which model is adapted for input of parameters thereinto and operative to simulate a functional process with these parameters, and wherein the data sets of individual functional processes are stored in the program library.

25. The method of claim 16, wherein a plurality of data sets are input into the blood treatment apparatus for selection among them.

26. The method of claim 16, wherein an identification of a user is detected by an ID reader and the control device receives a data set in dependence on the detected identification.

27. The method of claim 16, wherein an identification of a patient is detected by an ID reader and the control device receives a data set in dependence on the detected identification.

28. The method of claim 16, wherein the presence of a specific consumption article in the blood treatment apparatus is detected by a sensor and, in dependence on the detection result, one or a plurality of data sets are selected by the control device.

29. The method of claim 16, wherein the setting of a specific type of treatment on the blood treatment apparatus is detected, and one or a plurality of data sets are selected by the control device in dependence on the detection result.

30. The method of claim 16, wherein, at start-up of the blood treatment apparatus, the program library included on a data carrier is automatically read into the control device of the blood treatment apparatus.

* * * * *